United States Patent
Allen et al.

(10) Patent No.: US 11,113,418 B2
(45) Date of Patent: Sep. 7, 2021

(54) DE-IDENTIFICATION OF ELECTRONIC MEDICAL RECORDS FOR CONTINUOUS DATA DEVELOPMENT

(71) Applicant: INTERNATIONAL BUSINESS MACHINES CORPORATION, Armonk, NY (US)

(72) Inventors: Corville O. Allen, Morrisville, NC (US); Aysu Ezen Can, Cary, NC (US); Roberto Delima, Apex, NC (US); Robert C. Sizemore, Fuquay-Varina, NC (US)

(73) Assignee: International Business Machines Corporation, Armonk, NY (US)

( * ) Notice: Subject to any disclaimer, the term of this patent is extended or adjusted under 35 U.S.C. 154(b) by 371 days.

(21) Appl. No.: 16/205,423

(22) Filed: Nov. 30, 2018

(65) Prior Publication Data
US 2020/0175203 A1   Jun. 4, 2020

(51) Int. Cl.
*G06F 7/04* (2006.01)
*G06F 21/62* (2013.01)
*G06F 16/81* (2019.01)
*H04N 7/16* (2011.01)
*G16H 10/60* (2018.01)

(52) U.S. Cl.
CPC .......... *G06F 21/6254* (2013.01); *G06F 16/81* (2019.01); *G16H 10/60* (2018.01)

(58) Field of Classification Search
CPC ...... G06F 21/6254; G06F 16/81; G16H 10/60
See application file for complete search history.

(56) References Cited

U.S. PATENT DOCUMENTS

| | | |
|---|---|---|
| 8,355,923 B2 | 1/2013 | Gervais |
| 8,649,552 B2 | 2/2014 | Balakrishnan |
| 9,195,853 B2 | 11/2015 | Fox |
| 9,349,026 B2 | 5/2016 | Gianniotis |

(Continued)

OTHER PUBLICATIONS

Douglass et al., "Computer-Assisted De-Identification of Free Text in the MIMIC II Database", Harvard-MIT Division of Health Sciences & Technology, 2004, 4 pages, Cambridge MA, USA.

(Continued)

*Primary Examiner* — Darshan I Dhruv
(74) *Attorney, Agent, or Firm* — Steven M. Bouknight

(57) ABSTRACT

A method for de-identifying protected health information (PHI) associated with electronic medical records (EMRs) based on a common analysis structure (CAS) is provided. The method may include detecting a system event associated with a system comprising the EMRs. The method may further include in response to detecting the system event, detecting a first CAS associated with the EMRs. The method may further include extracting first CAS data associated with the first CAS, wherein the first CAS data comprises unstructured data associated with the EMRs and normalized annotations based on CAS objects that are associated with the unstructured data. The method may further include obfuscating the unstructured data associated with the first CAS. The method may also include generating a second CAS comprising the obfuscated unstructured data and a copied version of the normalized annotations, wherein the copied version of normalized annotations are correlated with the obfuscated unstructured data.

20 Claims, 6 Drawing Sheets

(56) References Cited

U.S. PATENT DOCUMENTS

| | | | |
|---|---|---|---|
| 2007/0078686 A1* | 4/2007 | Dettinger | G06Q 40/08 705/3 |
| 2007/0255704 A1* | 11/2007 | Baek | G06F 21/6254 |
| 2011/0162084 A1* | 6/2011 | Fox | G06F 21/6245 726/28 |
| 2011/0277037 A1* | 11/2011 | Burke | G06F 21/60 726/26 |
| 2013/0080398 A1* | 3/2013 | Booth | G06F 21/6254 707/687 |
| 2013/0091106 A1* | 4/2013 | Dubbels | G16H 30/40 707/694 |
| 2013/0167245 A1* | 6/2013 | Birtwhistle | G06F 21/6254 726/26 |
| 2015/0169895 A1* | 6/2015 | Gkoulalas-Divanis | G06F 21/6254 726/26 |
| 2015/0370979 A1* | 12/2015 | Boloor | G16H 40/20 705/3 |
| 2016/0117522 A1* | 4/2016 | Bhagwan | G06F 21/6245 726/28 |
| 2016/0321468 A1* | 11/2016 | Stankiewicz | G06F 21/6254 |
| 2016/0335397 A1* | 11/2016 | Blum | G06F 21/6254 |
| 2017/0076043 A1* | 3/2017 | Dormer | G06F 21/6218 |
| 2017/0286381 A1* | 10/2017 | Fink | G06F 3/0485 |
| 2018/0232488 A1* | 8/2018 | Jafer | G06F 21/6254 |
| 2019/0026435 A1* | 1/2019 | Benoni | G16H 10/60 |
| 2019/0102451 A1* | 4/2019 | Padgett | G06F 16/313 |
| 2020/0026875 A1* | 1/2020 | Leibovici | G06F 21/6245 |
| 2020/0143267 A1* | 5/2020 | Gidney | H04L 63/123 |
| 2020/0184100 A1* | 6/2020 | Ong | G06F 9/44505 |
| 2021/0012883 A1* | 1/2021 | Bidulock | G16H 40/20 |

OTHER PUBLICATIONS

Erdal, "De-Identified Multidimensional Medical Records for Disease Population Demographics and Image Processing Tools Development", Electrical and Computer Engineering, The Ohio State University, 2011, 131 pages.

Ferrandez et al., "BoB, a best-of-breed automated text de-identification system for VHA clinical documents", Research and applications, J Am Med Inform Assoc 2013, 7 pages.

Gardner et al., "HIDE: An Integrated System for Health Information DE-identification", 21st IEEE International Symposium on Computer-Based Medical Systems, 6 pages.

McMurry, "Distributed analyses of disease risk and association across networks of de-identified medical systems", Boston University Theses & Dissertations, 2015, 160 pages.

Mell et al., "The NIST Definition of Cloud Computing", National Institute of Standards and Technology, Special Publication 800-145, Sep. 2011, pp. 1-7.

Meystre et al., "Automatic de-identification of textual documents in the electronic health record: a review of recent research", BMC Medical Research Methodology, 2010, 16 pages, http://www.biomedcentral.com/1471-2288/10/70.

Neamatullah et al., "Automated de-identification of free-text medical records", BMC Medical Informatics and Decision Making, Jul. 24, 2008, 17 pages, http://www.biomedcentral.com/1472-6947/8/32.

Uzuner et al., "Evaluating the State-of-the-Art in Automatic De-identification", Journal of the American Medical Informatics Association, 2 pages, vol. 14, Issue 5, Sep.-Oct. 2007.

Wellner et al., "Rapidly Retargetable Approaches to De-identification in Medical Records", Journal of the American Medical Informatics Association vol. 14 No. 5, J Am Med Inform Assoc. 2007, 17 pages.

Dorr, et al., "Assessing the Difficulty and Time Cost of De-Identification in Clinical Narratives," Thieme E-Journals—Methods of Information in Medicine / Abstract, 2006; 45(03): 246-252, accessed Apr. 15, 2021, pp. 1-3, Retrieved from the Internet <https://www.thieme-connect.de/products/ejournals/abstract/10.1055/s-0038-1 634080>.

* cited by examiner

DE-IDENTIFICATION OF ELECTRONIC MEDICAL RECORDS FOR CONTINUOUS DATA DEVELOPMENT

BACKGROUND

The present invention relates generally to the field of computing, and more specifically, to data processing and management.

Protected Health Information (PHI) is an important part of medical text. PHI may generally refer to demographic information, medical histories, test and laboratory results, mental health conditions, insurance information, and other data that a healthcare professional collects to identify an individual and determine appropriate care. Typically, such information may be digitized and recorded in electronic medical records (EMR). Specifically, EMRs may contain information with PHI that is collected by and for clinicians in an office, clinic, or hospital, and are mostly used by providers for diagnosis and treatment. Furthermore, EMRs enable providers to track data over time, identify patients for preventive visits and screenings, monitor patients, and improve health care quality. However, during developmental processes, developers of electronic medical domains typically need to see the text contained in the EMR to be able to apply natural language understanding algorithms and evaluate the results. Furthermore, due to an event such as a system failure to a system containing EMRs, developers may need access to the data contained in the EMRs for debugging purposes. In such a case, de-identification of PHI is very important, due in part to different laws and regulations.

SUMMARY

A method de-identifying protected health information (PHI) associated with electronic medical records (EMRs) based on a common analysis structure (CAS) is provided. The method may include detecting a system event associated with a system comprising the electronic medical records (EMRs). The method may further include in response to detecting the system event, detecting a first common analysis structure (CAS) associated with the EMRs. The method may further include extracting first CAS data associated with the first CAS from one or more log files, wherein the first CAS data comprises unstructured data associated with the EMRs and comprises normalized annotations based on CAS objects that are associated with the unstructured data. The method may further include obfuscating the unstructured data associated with the first CAS based on the extracted first CAS data. The method may also include generating a second CAS comprising the obfuscated unstructured data and a copied version of the normalized annotations, wherein the copied version of normalized annotations are correlated with the obfuscated unstructured data.

A computer system for de-identifying protected health information (PHI) associated with electronic medical records (EMRs) based on a common analysis structure (CAS) is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include detecting a system event associated with a system comprising the electronic medical records (EMRs). The method may further include in response to detecting the system event, detecting a first common analysis structure (CAS) associated with the EMRs. The method may further include extracting first CAS data associated with the first CAS from one or more log files, wherein the first CAS data comprises unstructured data associated with the EMRs and comprises normalized annotations based on CAS objects that are associated with the unstructured data. The method may further include obfuscating the unstructured data associated with the first CAS based on the extracted first CAS data. The method may also include generating a second CAS comprising the obfuscated unstructured data and a copied version of the normalized annotations, wherein the copied version of normalized annotations are correlated with the obfuscated unstructured data.

A computer program product for de-identifying protected health information (PHI) associated with electronic medical records (EMRs) based on a common analysis structure (CAS) is provided. The computer program product may include one or more computer-readable storage devices and program instructions stored on at least one of the one or more tangible storage devices, the program instructions executable by a processor. The computer program product may include program instructions to detect a system event associated with a system comprising the electronic medical records (EMRs). The computer program product may further include program instructions to, in response to detecting the system event, detect a first common analysis structure (CAS) associated with the EMRs. The computer program product may also include program instructions to extract first CAS data associated with the first CAS from one or more log files, wherein the first CAS data comprises unstructured data associated with the EMRs and comprises normalized annotations based on CAS objects that are associated with the unstructured data. The computer program product may further include program instructions to obfuscate the unstructured data associated with the first CAS based on the extracted first CAS data. The computer program product may also include program instructions to generate a second CAS comprising the obfuscated unstructured data and a copied version of the normalized annotations, wherein the copied version of normalized annotations are correlated with the obfuscated unstructured data.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
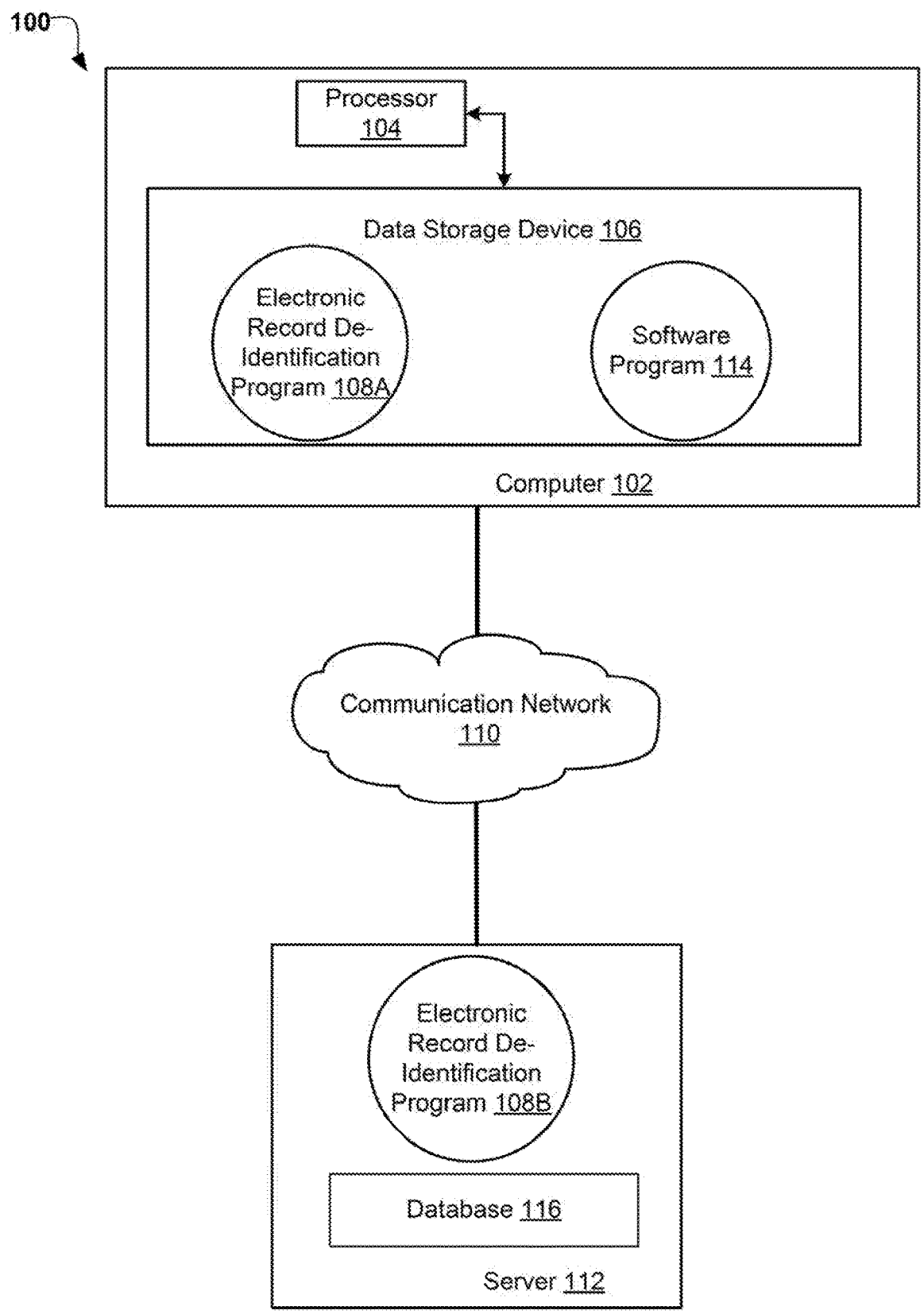
FIG. 1 illustrates a networked computer environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate generally to the field of computing, and more particularly, to data processing and management. The following described exemplary embodiments provide a system, method and program product for de-identifying protected health information (PHI) associated with electronic medical records (EMRs) based on a common analysis structure (CAS). Specifically, the present embodiment has the capacity to improve the technical field associated with medical databases by removing PHI in a reliable, automated and fast way to enable developers and users to develop and test system databases without the threat of viewing patient records. More specifically, the system, method and program product may de-identify EMRs by a process that generates a common analysis structure (CAS) comprising obfuscated unstructured data associated the EMRs as well as normalized annotations that are PHI-free.

As previously described with respect to data processing and management, electronic medical records (EMRs) may include digitized data containing protected health information (PHI) that is collected for diagnosis and treatment. Because PHI may generally include demographic information, medical histories, test and laboratory results, mental health conditions, insurance information, and other sensitive data, protecting such information is in imperative. However, developers often need to see the text that may be contained in EMRs in order to develop natural language understanding algorithms and to evaluate the algorithm results. Furthermore, due to events like a system failure to a database containing EMRs, developers may also need to access the database data for debugging purposes. For these types of situations, de-identification of the PHI is necessary in order to limit the threat leaking patient information. As such, it may be advantageous, among other things, to provide a method, system, and program product for removing PHI in a reliable, automated and fast way to enable developers and support personnel to develop and test system databases. Specifically, the system, method, and program product may de-identify protected health information (PHI) associated with patient records based on data associated with a common analysis structure (CAS).

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product for de-identifying protected health information (PHI) associated with electronic medical records (EMRs) based on a common analysis structure (CAS).

Referring now to FIG. 1, an exemplary networked computer environment 100 in accordance with one embodiment is depicted. The networked computer environment 100 may include a computer 102 with a processor 104 and a data storage device 106 that is enabled to run an electronic record de-identification program 108A and a software program 114 and may also include a microphone (not shown). The software program 114 may be an application program such as an internet browser and a question answering application. The electronic record de-identification program 108A may communicate with the software program 114. The networked computer environment 100 may also include a server 112 that is enabled to run an electronic record de-identification program 108B and the communication network 110. The networked computer environment 100 may include a plurality of computers 102 and servers 112, only one of which is shown for illustrative brevity.

According to at least one implementation, the present embodiment may also include a database 116, which may be running on server 112. The communication network 110 may include various types of communication networks, such as a wide area network (WAN), local area network (LAN), a telecommunication network, a wireless network, a public switched network and/or a satellite network. It may be appreciated that FIG. 1 provides only an illustration of one implementation and does not imply any limitations with regard to the environments in which different embodiments may be implemented. Many modifications to the depicted environments may be made based on design and implementation requirements.

The client computer 102 may communicate with server computer 112 via the communications network 110. The communications network 110 may include connections, such as wire, wireless communication links, or fiber optic cables. As will be discussed with reference to FIG. 3, server computer 112 may include internal components 800a and external components 900a, respectively, and client computer 102 may include internal components 800b and external components 900b, respectively. Server computer 112 may also operate in a cloud computing service model, such as Software as a Service (SaaS), Platform as a Service (PaaS), or Infrastructure as a Service (IaaS). Server 112 may also be located in a cloud computing deployment model, such as a private cloud, community cloud, public cloud, or hybrid cloud. Client computer 102 may be, for example, a mobile device, a telephone, a personal digital assistant, a netbook, a laptop computer, a tablet computer, a desktop computer, or any type of computing device capable of running a program and accessing a network. According to various implementations of the present embodiment, the electronic record de-identification program 108A, 108B may interact with a database 116 that may be embedded in various storage devices, such as, but not limited to, a mobile device 102, a networked server 112, or a cloud storage service.

According to the present embodiment, a program, such as an electronic record de-identification program 108A and 108B may run on the client computer 102 or on the server computer 112 via a communications network 110. The electronic record de-identification program 108A, 108B may provide an electronic record de-identification system for presenting structured answers to a received query. Specifically, a user using a computer, such as computer 102, may run an electronic record de-identification program 108A, 108B, that may interact with a database 116 and a software program 114, to de-identifying protected health information (PHI) associated with electronic medical records (EMRs) based on a common analysis structure (CAS). More specifically, the electronic record de-identification program 108A, 108B may de-identify EMRs based on a process that generates a common analysis structure (CAS) that comprises obfuscated unstructured data associated the EMRs as well as normalized annotations that are PHI-free.

As previously described, electronic medical records (EMRs) may include digitized information containing protected health information (PHI) that is collected for diagnosis and treatment. For computers and computer analysis, however, this digitized information is typically unstructured information. Specifically, in contrast to structured information, whose meaning is expressed by the structure or format of the data (such as data organized in a database table), the meaning of unstructured information cannot be so inferred. More specifically, examples of data that carry unstructured information include natural language text and data from audio or video sources. As such, the natural language text associated with patient records, which may include PHI, is unstructured information. However, through an unstructured information management architecture (UIMA), large volumes of unstructured information may be analyzed to discover, organize, and deliver relevant knowledge.

Specifically, using the UIMA, unstructured information may be analyzed to interpret, detect, and locate concepts of interest that are not structurally tagged or annotated in the original document. For example, documents like a clinician's notes may include domain-specific information such as: named entities (persons, organizations, locations, facilities, or products), opinions (complaints, diagnosis, or facts), and relations (finances, insurance info). The UIMA may organize such data through the use of a common analysis structure (CAS) in order to represent the data in a more structured manner. The Common Analysis Structure (CAS) is an object-based data structure that is typically a subsystem of the UIMA. The CAS may logically represent the natural language text through objects, properties, and values. In turn, an arbitrary data structure may be created and stored, and may represent the analysis of the natural language text. For example, a CAS may logically analyze statements in a document that includes objects of a person type (such as a person's name). Therefore, for each person that is found in the body of a document, the analysis engine creates a Person object in the CAS and links it to the span of text where the person is mentioned in the document. These created objects may essentially represent normalized annotations of certain text within a document based on the CAS.

In the case of EMRs, the CAS objects may represent the findings on a particular set of patient records. Furthermore, the unstructured data included in the digitized information (i.e. in EMRs) may contain PHI, but the annotations derived from the CAS are normalized in a fashion that is PHI-free. Typically, the CAS, which contains the CAS objects (i.e. the normalized annotations) and the unstructured data that the CAS objects are based on, gets written to log files. Thus, due to the unstructured data, the information in the log files may typically contain PHI that needs to be obfuscated. As such, the present invention may generate a CAS using the metadata associated with the log files and may de-identify the PHI information contained within the log files based on a process described herewith. In turn, developers may be enabled to troubleshoot issues associated with the system/database without the risk of accessing the PHI.

Figure 2:
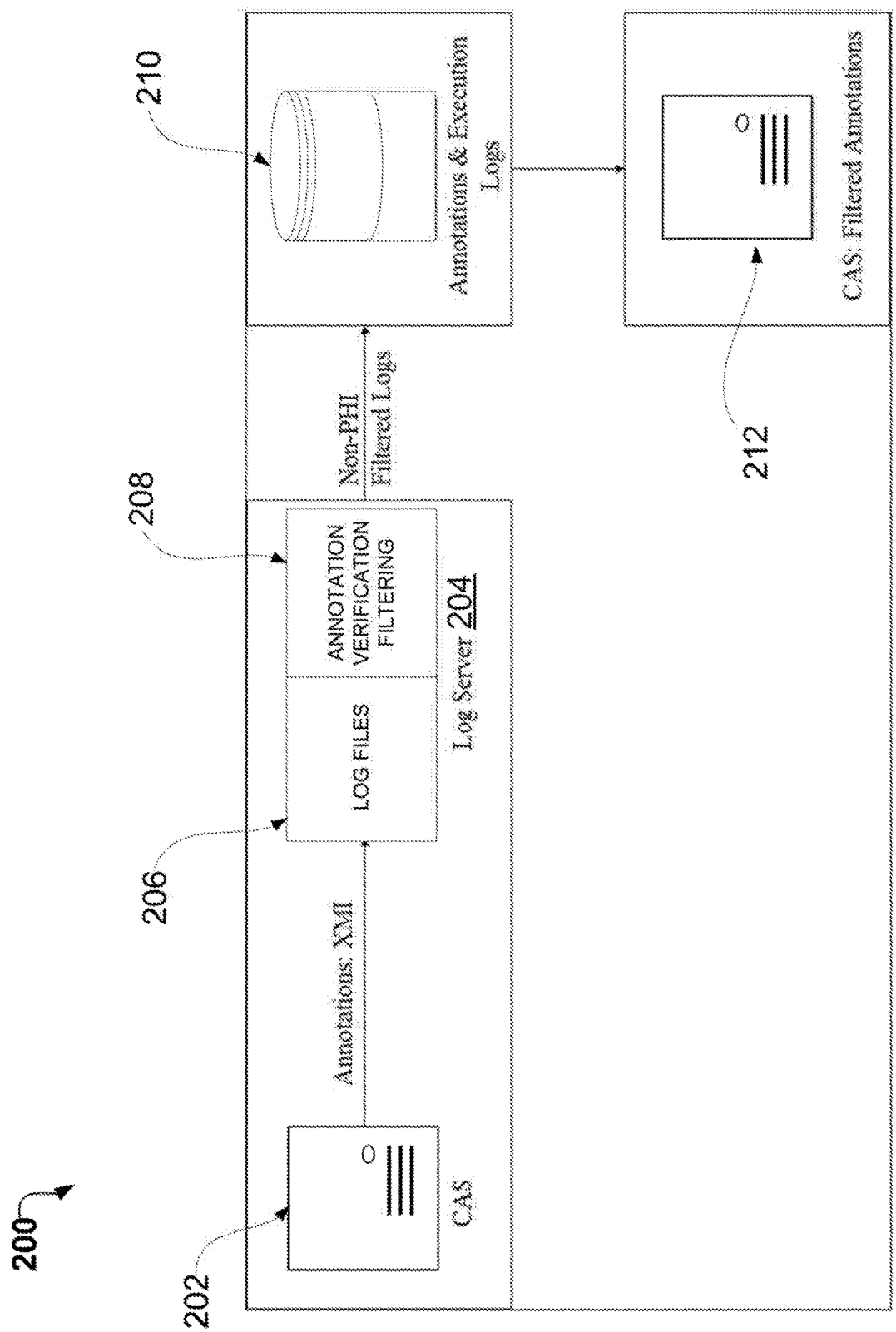
FIG. 2 is a block diagram illustrating a program for de-identifying protected health information (PHI) associated with electronic medical records (EMRs) based on a common analysis structure (CAS) according to one embodiment.

Referring now to FIG. 2, a block diagram 200 illustrating an electronic record de-identification program 108A, 108B (FIG. 1) for de-identifying protected health information (PHI) associated with electronic medical records (EMRs) based on a common analysis structure (CAS) according to one embodiment is depicted. Specifically, according to one embodiment, the electronic record de-identification program 108A, 108B (FIG. 1) may collect data associated with a common analysis structure (CAS) 202. More specifically, in response to an event such as a system failure or a request to access EMRs for developmental testing, the electronic record de-identification program 108A, 108B (FIG. 1) may identify a CAS 202 associated with electronic medical records (EMRs). Thereafter, the electronic record de-identification program 108A, 108B (FIG. 1) may collect the data associated with the CAS 202, whereby the collected data may include the normalized annotations associated with the EMRs as well as the unstructured data associated with the EMRs, with which the CAS 202 is based. Specifically, the normalized annotations may include XML Metadata Interchange (XMI) files as depicted in FIG. 2. The XML Metadata Interchange (XMI) files is an Object Management Group (OMG) standard for exchanging metadata information via Extensible Markup Language (XML).

As previously described, the unstructured data may contain PHI, but the annotations derived from the CAS 202 are normalized in a fashion that is PHI-free. In case of an event such as a failure to a system or a database containing EMRs, the normalized annotations and the unstructured data gets written to log files. Therefore, the electronic record de-identification program 108A, 108B (FIG. 1) may collect the data associated with the CAS 202 from a server, such as log server 204, whereby the log server 204 may include log files 206 that are associated with the CAS 202, and whereby the CAS 202 includes the normalized annotations and the unstructured data. The electronic record de-identification program 108A, 108B (FIG. 1) may also include an annotation verification filtering 208 to identify and interrogate the normalized annotations and to de-identify the unstructured data that the CAS 202 is based on. The electronic record de-identification program 108A, 108B (FIG. 1) may store the filtered logs of the copied and collected CAS data at annotations and execution logs 210. In turn, at CAS filtered annotations 212, based on the copied and collected data, the electronic record de-identification program 108A, 108B (FIG. 1) may generate and store a new CAS comprising the filtered normalized annotations associated with the CAS 202 that are PHI-free, as well as the de-identified unstructured data based on the following described process in FIG. 3 for filtering the unstructured data. The CAS filtered annotations 212 may further correlate the filtered normalized annotations associated with the CAS 202 that are PHI-free with the de-identified unstructured data. As such, the generated CAS may be used by developers in response to the system failure and/or to test the system.

Figure 3:
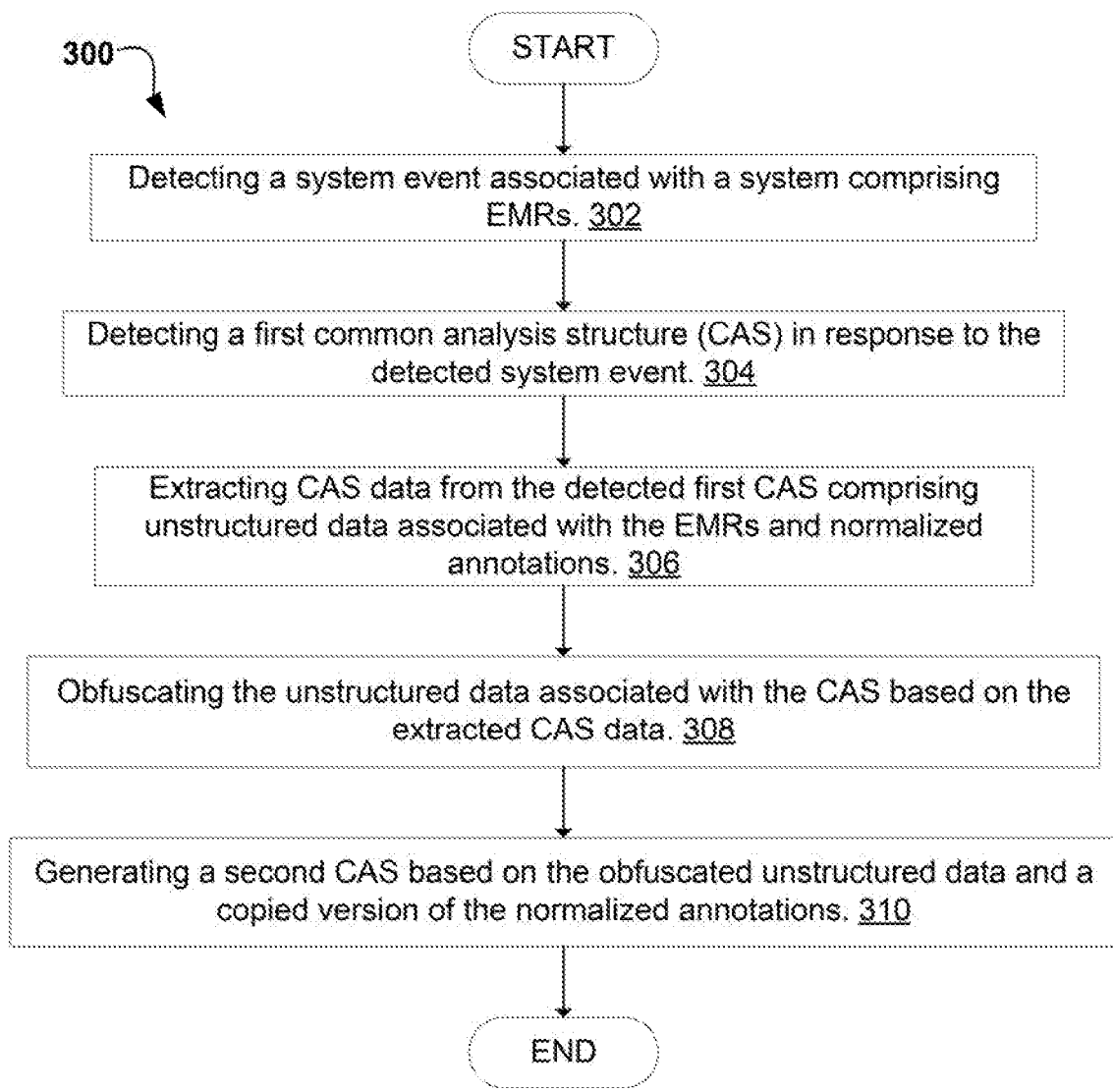
FIG. 3 is an operational flowchart illustrating the steps carried out by a program for de-identifying protected health information (PHI) associated with electronic medical records (EMRs) based on a common analysis structure (CAS)

Referring now to FIG. 3, an operational flowchart 300 illustrating the steps carried out by a program for de-identifying protected health information (PHI) associated with patient records based on a common analysis structure (CAS) is depicted. At 302, the electronic record de-identification program 108A, 108B (FIG. 1) may detect a system event, whereby the system event is associated with a system comprising electronic medical records (EMRs). More specifically, the system event may include, for example, a request to access the EMRs from a developer needing access to the text associated with the EMRs in order to develop natural language understanding algorithms and to evaluate the algorithm results. Also, for example, the system event may include a system failure to a database containing EMRs, and a need for developers to access the database data for debugging purposes.

Next, at 304, in response to detecting the system event, the electronic record de-identification program 108A, 108B (FIG. 1) may detect a common analysis structure (CAS)

associated with the EMRs that are based on the system event. As previously described, the natural language text associated with EMRs may include PHI, and this natural language text is considered unstructured information. The CAS 202 may logically represent the unstructured information as objects, properties, and values. In turn, the CAS 202 may create and store an object-based data structure that logically represents the unstructured data associated with the EMRs. More specifically, this object-based data structure may include created CAS objects that represent normalized annotations of certain text within the EMRs. Thus, the CAS 202 may include the unstructured data, or text, associated with the EMRs as well as the normalized annotations (i.e. the CAS objects). As such, in response to the system event, the electronic record de-identification program 108A, 108B (FIG. 1) may detect this CAS 202 associated with the EMRs in response to the system event.

Then, at 306, the electronic record de-identification program 108A, 108B (FIG. 1) may extract the data associated with the CAS 202 from log files 206. As previously described, CAS data, including the CAS objects and the unstructured data, gets written to log files 206. For example, the unstructured data and the normalized annotations that are based on the CAS may be included in XML Metadata Interchange (XMI) files. As previously described, the XML Metadata Interchange (XMI) files is an Object Management Group (OMG) standard for exchanging metadata information via Extensible Markup Language (XML). As such, the electronic record de-identification program 108A, 108B (FIG. 1) may extract the data associated with the log files 206 from a log server 204. Furthermore, the extracted data may include metadata that is associated with the CAS 202.

Next, at 308, the electronic record de-identification program 108A, 108B (FIG. 1) may obfuscate the extracted unstructured data associated with the CAS 202. Specifically, according to one embodiment, the electronic record de-identification program 108A, 108B (FIG. 1) may copy the unstructured data/text from the CAS 202, and may obfuscate the extracted unstructured data associated with the CAS 202 by replacing all alphanumeric characters associated with the unstructured data/text with a pre-designated character, such as, for example, replacing the alphanumeric characters with the variable "X".

Then, at 310, the electronic record de-identification program 108A, 108B (FIG. 1) may generate a second CAS 212 based on the obfuscated unstructured data/text and by copying the normalized annotations associated with the CAS 202. Specifically, according to one embodiment, the electronic record de-identification program 108A, 108B (FIG. 1) may copy the normalized annotations using a log correlation process that essentially interrogates the normalized annotations based on natural language techniques to further detect whether the normalized annotations contain protected health information (PHI) as the normalized annotations are copied. The electronic record de-identification program 108A, 108B (FIG. 1) may also correlate the copied normalized annotations with the obfuscated unstructured data/text using associated universally unique identifiers (UUIDs). As previously described, the unstructured data included in EMRs may contain PHI, but the annotations derived from the CAS 202 are normalized in a fashion that is PHI-free. Also, and as previously described in FIG. 2, the electronic record de-identification program 108A, 108B (FIG. 1) may include an annotation verification filtering system 208 to copy the normalized annotations, detect whether the copied normalized annotations contain PHI, and to de-identify the unstructured data that the CAS 202 is based on. As such, the logging process used by the electronic record de-identification program 108A, 108B (FIG. 1) may reassure that there is no leakage of PHI in the normalized annotations. This logging process may be repeated until all the normalized annotations are processed.

Then, the electronic record de-identification program 108A, 108B (FIG. 1) may store the processed normalized annotations data associated with the normalized annotations and the obfuscated unstructured data in annotations and execution logs 210. Thereafter, based on the stored data, the electronic record de-identification program 108A, 108B (FIG. 1) may generate the second CAS comprising the obfuscated unstructured data/text as well as the copied and processed normalized annotations data. As such, the present invention may rebuild the CAS 202 using the metadata associated with the log files 206 and may de-identify the PHI information contained within the EMRs. Therefore, the electronic record de-identification program 108A, 108B (FIG. 1) may enable usage of the generated CAS, comprising the copied normalized annotations and the de-identified unstructured data associated with the EMRs, by developers in response to the system event.

It may be appreciated that FIGS. 2 and 3 provide only illustrations of one implementation and does not imply any limitations with regard to how different embodiments may be implemented. Many modifications to the depicted environments may be made based on design and implementation requirements.

Figure 4:
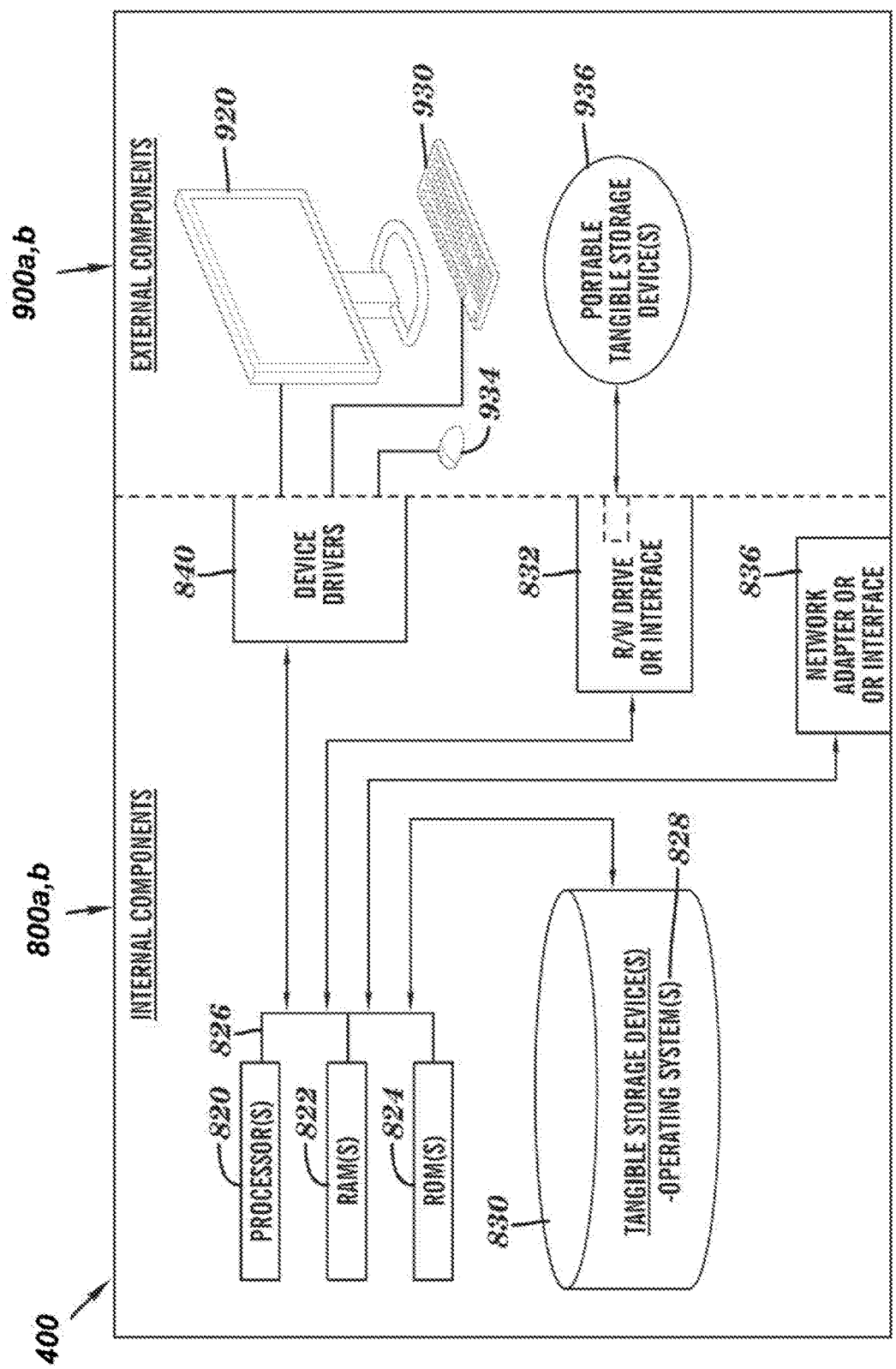
FIG. 4 is a block diagram of the system architecture of a program for de-identifying protected health information (PHI) associated with electronic medical records (EMRs) based on a common analysis structure (CAS) according to one embodiment.

FIG. 4 is a block diagram 400 of internal and external components of computers depicted in FIG. 1 in accordance with an illustrative embodiment of the present invention. It should be appreciated that FIG. 4 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

User client computer 102 (FIG. 1), and network server 112 (FIG. 1) include respective sets of internal components 800 a, b and external components 900 a, b illustrated in FIG. 4. Each of the sets of internal components 800 a, b includes one or more processors 820, one or more computer-readable RAMs 822, and one or more computer-readable ROMs 824 on one or more buses 826, and one or more operating systems 828 and one or more computer-readable tangible storage devices 830. The one or more operating systems 828, the software program 114 (FIG. 1) and the electronic record de-identification program 108A (FIG. 1) in client computer 102 (FIG. 1), and the electronic record de-identification program 108B (FIG. 1) in network server computer 112 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 4, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 a, b, also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as an electronic record de-identification program 108A and 108B (FIG. 1), can be stored on one or more of the respective portable computer-readable tangible storage devices 936, read via the respective R/W drive or interface 832, and loaded into the respective hard drive 830.

Each set of internal components 800 a, b also includes network adapters or interfaces 836 such as a TCP/IP adapter cards, wireless Wi-Fi interface cards, or 3G or 4G wireless interface cards or other wired or wireless communication links. The electronic record de-identification program 108A (FIG. 1) and software program 114 (FIG. 1) in client computer 102 (FIG. 1), and the electronic record de-identification program 108B (FIG. 1) in network server 112 (FIG. 1) can be downloaded to client computer 102 (FIG. 1) from an external computer via a network (for example, the Internet, a local area network or other, wide area network) and respective network adapters or interfaces 836. From the network adapters or interfaces 836, the electronic record de-identification program 108A (FIG. 1) and software program 114 (FIG. 1) in client computer 102 (FIG. 1) and the electronic record de-identification program 108B (FIG. 1) in network server computer 112 (FIG. 1) are loaded into the respective hard drive 830. The network may comprise copper wires, optical fibers, wireless transmission, routers, firewalls, switches, gateway computers, and/or edge servers.

Each of the sets of external components 900 a, b can include a computer display monitor 920, a keyboard 930, and a computer mouse 934. External components 900 a, b can also include touch screens, virtual keyboards, touch pads, pointing devices, and other human interface devices. Each of the sets of internal components 800a, b also includes device drivers 840 to interface to computer display monitor 920, keyboard 930, and computer mouse 934. The device drivers 840, R/W drive or interface 832, and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 5:
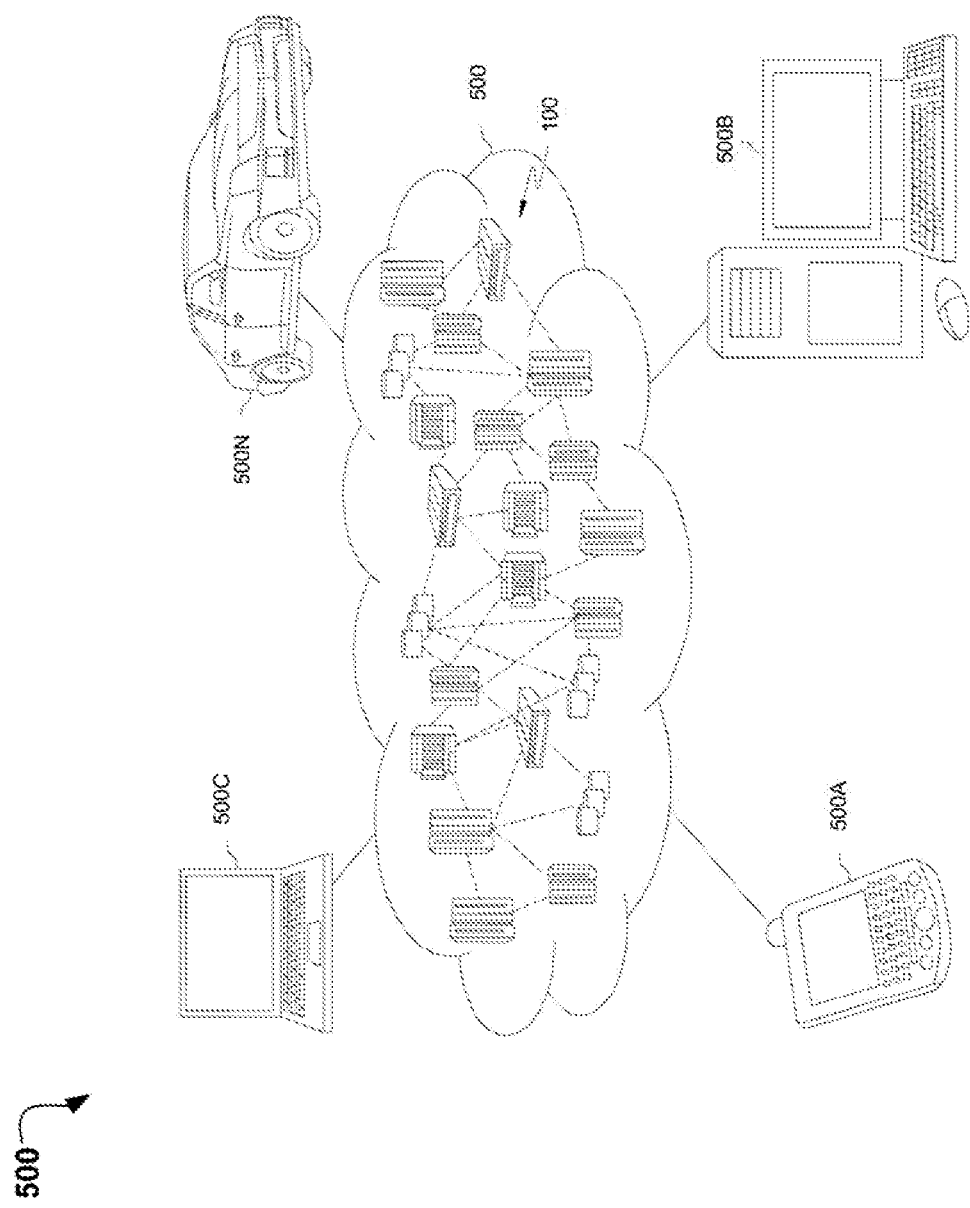
FIG. 5 is a block diagram of an illustrative cloud computing environment including the computer system depicted in FIG. 1, in accordance with an embodiment of the present disclosure.

Referring now to FIG. 5, illustrative cloud computing environment 500 is depicted. As shown, cloud computing environment 500 comprises one or more cloud computing nodes 100 with which local computing devices used by cloud consumers, such as, for example, personal digital assistant (PDA) or cellular telephone 500A, desktop computer 500B, laptop computer 500C, and/or automobile computer system 500N may communicate. Nodes 100 may communicate with one another. They may be grouped (not shown) physically or virtually, in one or more networks, such as Private, Community, Public, or Hybrid clouds as described hereinabove, or a combination thereof. This allows cloud computing environment 500 to offer infrastructure, platforms and/or software as services for which a cloud consumer does not need to maintain resources on a local computing device. It is understood that the types of computing devices 500A-N shown in FIG. 5 are intended to be illustrative only and that computing nodes 100 and cloud computing environment 500 can communicate with any type of computerized device over any type of network and/or network addressable connection (e.g., using a web browser).

Figure 6:
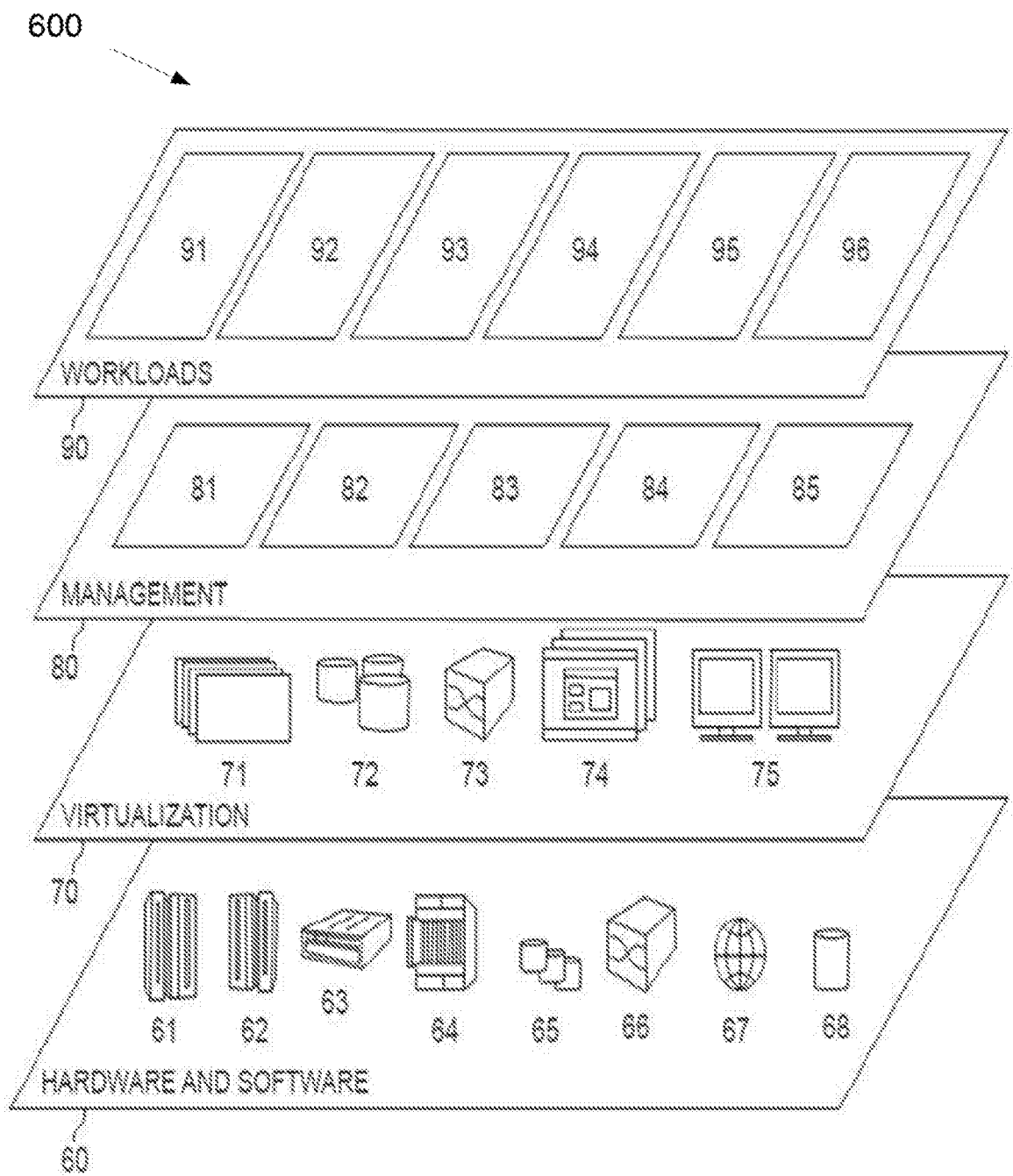
FIG. 6 is a block diagram of functional layers of the illustrative cloud computing environment of FIG. 5, in accordance with an embodiment of the present disclosure.

Referring now to FIG. 6, a set of functional abstraction layers 600 provided by cloud computing environment 500 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and electronic record de-identification 96. An electronic record de-identification program 108A, 108B (FIG. 1) may be offered "as a service in the cloud" (i.e., Software as a Service (SaaS)) for applications running on computing devices 102 (FIG. 1) and may de-identify protected health information (PHI) associated with patient records based on a common analysis structure (CAS).

The descriptions of the various embodiments of the present invention have been presented for purposes of illustration but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for providing de-identified protected health information (PHI) associated with electronic medical records (EMRs) based on a common analysis structure (CAS), the method comprising:

generating a first common analysis structure (CAS) for representing the PHI associated with the EMRs, wherein generating the first CAS comprises logically representing unstructured data associated with the EMRs and including the PHI as objects to create an object-based data structure associated with the electronic medical records (EMRs), wherein the objects comprise normalized annotations;

in response to detecting a system event, extracting first CAS data associated with the first CAS from one or more log files, wherein the first CAS data comprises the unstructured data and the normalized annotations based on the objects that are associated with the unstructured data;

obfuscating the unstructured data associated with the first CAS based on the extracted first CAS data; and generating and providing a second CAS comprising the obfuscated unstructured data and a copied version of the normalized annotations, wherein the copied version of the normalized annotations are correlated with the obfuscated unstructured data.

2. The method of claim 1, wherein the system event is selected from a group comprising a request to access the EMRs and a system failure.

3. The method of claim 1, wherein the extracted first CAS data comprises extracted XML Metadata Interchange (XMI) files.

4. The method of claim 1, wherein obfuscating the identified unstructured data further comprises:
   replacing each alphanumeric character associated with the unstructured data with a designated character.

5. The method of claim 1, wherein the copied version of normalized annotations are copied based on a log correlation process that detects whether the copied version of the normalized annotations include the protected health information (PHI) as the normalized annotations are copied.

6. The method of claim 1, wherein the copied version of the normalized annotations are correlated with the obfuscated unstructured data using associated universally unique identifiers (UUIDs).

7. The method of claim 1, further comprising:
   enabling usage of the generated second CAS in response to the detected system event.

8. A computer system for providing de-identified protected health information (PHI) associated with electronic medical records (EMRs) based on a common analysis structure (CAS), comprising:
   one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:
   generating a first common analysis structure (CAS) for representing the PHI associated with the EMRs, wherein generating the first CAS comprises logically representing unstructured data associated with the EMRs and including the PHI as objects to create an object-based data structure associated with the electronic medical records (EMRs), wherein the objects comprise normalized annotations;
   in response to detecting a system event, extracting first CAS data associated with the first CAS from one or more log files, wherein the first CAS data comprises the unstructured data and the normalized annotations based on the objects that are associated with the unstructured data;
   obfuscating the unstructured data associated with the first CAS based on the extracted first CAS data; and
   generating and providing a second CAS comprising the obfuscated unstructured data and a copied version of the normalized annotations, wherein the copied version of the normalized annotations are correlated with the obfuscated unstructured data.

9. The computer system of claim 8, wherein the system event is selected from a group comprising a request to access the EMRs and a system failure.

10. The computer system of claim 8, wherein the extracted first CAS data comprises extracted XML Metadata Interchange (XMI) files.

11. The computer system of claim 8, wherein obfuscating the identified unstructured data further comprises:
    replacing each alphanumeric character associated with the unstructured data with a designated character.

12. The computer system of claim 8, wherein the copied version of normalized annotations are copied based on a log correlation process that detects whether the copied version of the normalized annotations include the protected health information (PHI) as the normalized annotations are copied.

13. The computer system of claim 8, wherein the copied version of the normalized annotations are correlated with the obfuscated unstructured data using associated universally unique identifiers (UUIDs).

14. The computer system of claim 8, further comprising:
    enabling usage of the generated second CAS in response to the detected system event.

15. A computer program product for providing de-identified protected health information (PHI) associated with electronic medical records (EMRs) based on a common analysis structure (CAS), comprising:
    one or more computer-readable storage devices and program instructions stored on at least one of the one or more tangible storage devices, the program instructions executable by a processor, the program instructions comprising:
    program instructions to generate a first common analysis structure (CAS) for representing the PHI associated with the EMRs, wherein generating the first CAS comprises logically representing unstructured data associated with the EMRs and including the PHI as objects to create an object-based data structure associated with the electronic medical records (EMRs), wherein the objects comprise normalized annotations;
    in response to detecting a system event, program instructions to extract first CAS data associated with the first CAS from one or more log files, wherein the first CAS data comprises the unstructured data and the normalized annotations based on the objects that are associated with the unstructured data;
    program instructions to obfuscate the unstructured data associated with the first CAS based on the extracted first CAS data; and
    program instructions to generate and provide a second CAS comprising the obfuscated unstructured data and a copied version of the normalized annotations, wherein the copied version of the normalized annotations are correlated with the obfuscated unstructured data.

16. The computer program product of claim 15, wherein the system event is selected from a group comprising a request to access the EMRs and a system failure.

17. The computer program product of claim 15, wherein the extracted first CAS data comprises extracted XML Metadata Interchange (XMI) files.

18. The computer program product of claim 15, wherein the program instructions to obfuscate the identified unstructured data further comprises:
    program instructions to replace each alphanumeric character associated with the unstructured data with a designated character.

19. The computer program product of claim 15, wherein the copied version of normalized annotations are copied based on a log correlation process that detects whether the copied version of the normalized annotations include the protected health information (PHI) as the normalized annotations are copied.

20. The computer program product of claim 15, wherein the copied version of the normalized annotations are correlated with the obfuscated unstructured data using associated universally unique identifiers (UUIDs).

* * * * *